US011207080B2

(12) United States Patent
Kam et al.

(10) Patent No.: US 11,207,080 B2
(45) Date of Patent: Dec. 28, 2021

(54) ORTHOPEDIC DRILL BIT WITH SWIVELING HEAD

(71) Applicant: CONMED CORPORATION, Utica, NY (US)

(72) Inventors: Andrew Kam, Odessa, FL (US); Andrew P. Muser, St. Pete Beach, FL (US)

(73) Assignee: CONMED CORPORATION, Utica, NY (US)

( * ) Notice: Subject to any disclaimer, the term of this patent is extended or adjusted under 35 U.S.C. 154(b) by 96 days.

(21) Appl. No.: 16/621,805

(22) PCT Filed: Jun. 12, 2018

(86) PCT No.: PCT/US2018/036990
§ 371 (c)(1),
(2) Date: Dec. 12, 2019

(87) PCT Pub. No.: WO2018/231746
PCT Pub. Date: Dec. 20, 2018

(65) Prior Publication Data
US 2020/0170652 A1 Jun. 4, 2020

Related U.S. Application Data

(60) Provisional application No. 62/518,261, filed on Jun. 12, 2017.

(51) Int. Cl.
*A61B 17/16* (2006.01)
*A61B 17/56* (2006.01)

(52) U.S. Cl.
CPC .... *A61B 17/1617* (2013.01); *A61B 2017/564* (2013.01)

(58) Field of Classification Search
CPC . A61B 17/16; A61B 17/1613; A61B 17/1615; A61B 17/1617; A61B 17/1633; A61B 17/1662; A61B 17/1675
See application file for complete search history.

(56) References Cited

U.S. PATENT DOCUMENTS 5,928,239 A * 7/1999 Mirza ............ A61B 17/320725
606/79
8,591,514 B2 * 11/2013 Sherman ............ A61B 17/1617
606/80
(Continued)

FOREIGN PATENT DOCUMENTS

EP 2098177 9/2009
JP 2013-017610 A 4/2014
(Continued)

OTHER PUBLICATIONS

International Search Report Form PCT/ISA/220, International Application No. PCT/US2018/036990, pp. 1-12, dated Sep. 19, 2018.

*Primary Examiner* — Eric S Gibson
(74) *Attorney, Agent, or Firm* — Bond, Schoeneck & King, PLLC; Frederick J. M. Price

(57) ABSTRACT

An orthopedic drill bit that is configurable to form a first bone tunnel having a first bore when inserted through a bone and a second, larger bore as the drill is partially withdrawn from bone to produce a reverse counterbore for accepting an anchor. The drill bit has a shaft with a pivotal cutting tip that is movable from a narrow boring configuration into a wider boring configuration. The drill bit has a body enclosing the shaft that is biased into engagement with the cutting tip. Rotation of the body allow a user to move the cutting tip from the narrower bore configuration used to drill a pilot hole into a wider bore configuration used to drill a reverse counterbore for accepting the anchor.

5 Claims, 12 Drawing Sheets

(56) References Cited

U.S. PATENT DOCUMENTS

| | | | |
|---|---|---|---|
| 8,888,781 B2* | 11/2014 | Sterrett | A61B 17/3472 606/80 |
| 9,622,757 B2* | 4/2017 | Bourque | G01B 5/06 |
| 9,655,629 B2* | 5/2017 | Takeuchi | A61B 17/16 |
| 9,668,750 B2* | 6/2017 | Mirochinik | A61B 17/1796 |
| 10,492,800 B2* | 12/2019 | Papenfuss | A61B 17/1617 |
| 10,568,641 B1* | 2/2020 | Karasic | A61B 17/1622 |
| 10,695,073 B2* | 6/2020 | Adams | A61B 17/1624 |
| 2001/0034526 A1* | 10/2001 | Kuslich | A61B 17/1617 606/80 |
| 2005/0240193 A1* | 10/2005 | Layne | A61B 17/1671 606/80 |
| 2006/0195112 A1* | 8/2006 | Ek | A61B 17/1675 606/86 R |
| 2006/0241629 A1* | 10/2006 | Krebs | A61B 17/1631 606/80 |
| 2007/0123889 A1* | 5/2007 | Malandain | A61B 17/320016 606/79 |
| 2007/0276392 A1 | 11/2007 | Beyar et al. | |
| 2010/0268175 A1* | 10/2010 | Lunsford | A61B 17/3415 604/272 |
| 2011/0130760 A1* | 6/2011 | Anderson | A61B 17/1617 606/79 |
| 2011/0251616 A1* | 10/2011 | Osman | A61B 17/1671 606/80 |
| 2014/0257297 A1* | 9/2014 | Koogle, Jr. | A61B 17/1668 606/80 |
| 2014/0276844 A1* | 9/2014 | Bourque | A61B 17/1615 606/80 |
| 2015/0351777 A1* | 12/2015 | Lizardi | A61B 17/1622 606/80 |
| 2017/0143352 A1* | 5/2017 | Papenfuss | A61B 17/1617 |
| 2019/0059910 A1* | 2/2019 | Adams | A61B 17/1624 |
| 2020/0008814 A1* | 1/2020 | Muser | A61B 17/1617 |
| 2020/0170652 A1* | 6/2020 | Kam | A61B 17/1617 |

FOREIGN PATENT DOCUMENTS

| | | |
|---|---|---|
| JP | 2015-536736 A | 12/2015 |
| JP | 2016-511071 A | 4/2016 |
| WO | 2014/089198 | 6/2014 |

* cited by examiner

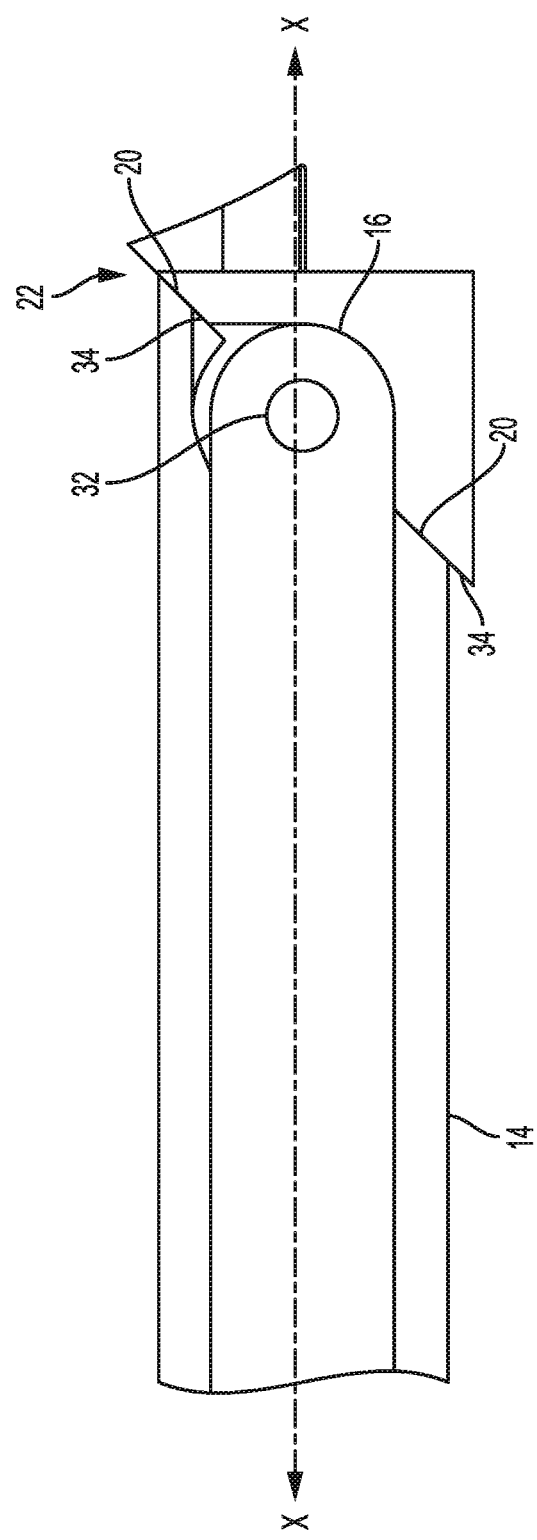
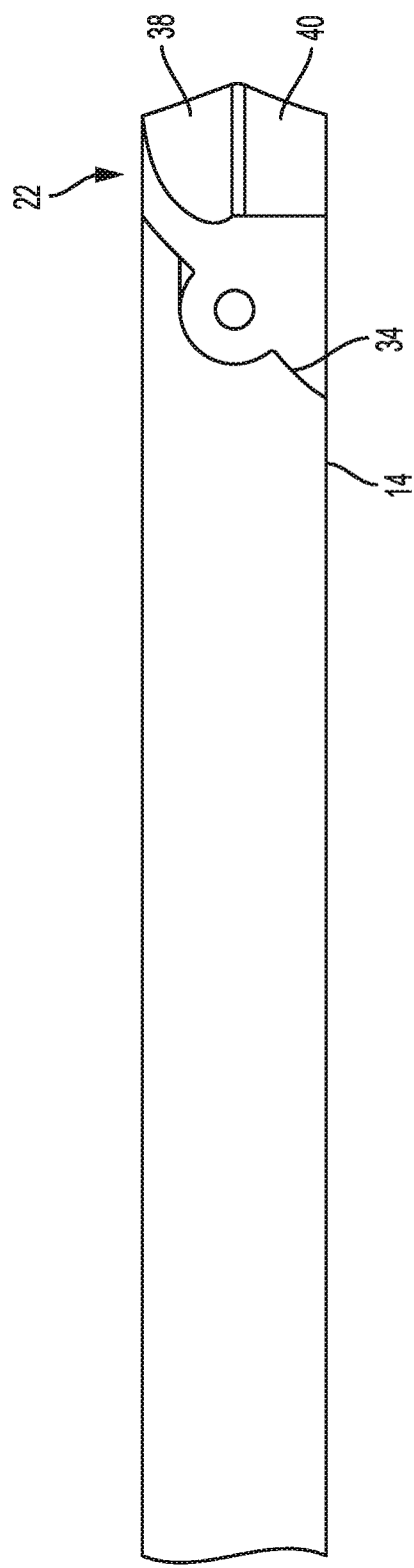

ORTHOPEDIC DRILL BIT WITH SWIVELING HEAD

CROSS-REFERENCE TO RELATED APPLICATIONS

The present application claims priority to U.S. Provisional No. 62/518,261, filed on Jun. 12, 2017.

BACKGROUND OF THE INVENTION

1. Field of the Invention

The present invention relates to orthopedic drills and, more particularly, to a orthopedic drill bit can produce a retrograde counterbore in a bone.

2. Description of the Related Art

Conventional orthopedic reconstruction surgeries often involve the drilling of a tunnel through a bone for the purposes of installing an anchor for a graft. For example, knee ligament reconstruction surgeries require a bone socket to be formed by drilling into the bone that will serve as the anchor for a ligament graft. Convention drilling procedures tend to remove more bone than is necessary as a tunnel of the appropriate diameter for receiving an anchor is drilled entirely through the anchoring bone. The unnecessary removal of bone can lead to more pain for the patient as well as a longer healing period. Accordingly, there is a need in the art for an approach that can produce an acceptable bone socket with minimal bone removal.

BRIEF SUMMARY OF THE INVENTION

The present invention is orthopedic drill bit that is configurable to form a first bone tunnel having a first bore with a first diameter as it is inserted through a bone and then a second bore having a second diameter that is larger than the first diameter as the drill is partially withdrawn from bone to produce a reverse counterbore for accepting an anchor and thus reducing the amount of material needed for securing a graft during an orthopedic surgery. The drill bit comprise a shaft extending along an axis and a cutting tip pivotally mounted to the shaft and moveable between a first position where the tip is aligned along the axis and a second position where the tip is perpendicular to the axis. The cutting tip in the first position defines a first bore having a first diameter and the cutting tip in the second position defines a second bore having a second diameter that is larger than the first diameter. The drill bit further comprises a body enclosing the shaft. The body is moveable along the axis and rotatable about the axis, and includes a cam surface extending at a first angle with respect to the axis. The cutting tip includes a bearing surface extending at a second angle with respect to the axis that is complementary to the first angle. The body is biased so that the cam surface can engage the bearing surface. The body is rotatable between a first orientation that moves the cutting tip into the first position and a second orientation that moves the cutting tip into the second position. The cutting tip is configured to having cutting surfaces that form the first bore and the second bore.

The present invention also includes a method of forming a bone tunnel using a drill bit having a shaft extending along an axis and a cutting tip pivotally mounted to the shaft and moveable between a first position where the tip is aligned along the axis and a second position where the tip is perpendicular to the axis to form a first bore. The drill bit is advanced through a bone with the cutting tip in the first position. The cutting tip of drill bit is then moved into the second position. The drill bit is then partially withdrawn though the first bore to form a second bore having the second diameter.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 2 is a cross-section of a drill bit according to the present invention;

FIG. 3 is a schematic of the cutting tip according to the present invention in a first position;

DETAILED DESCRIPTION OF THE INVENTION

Figure 1:
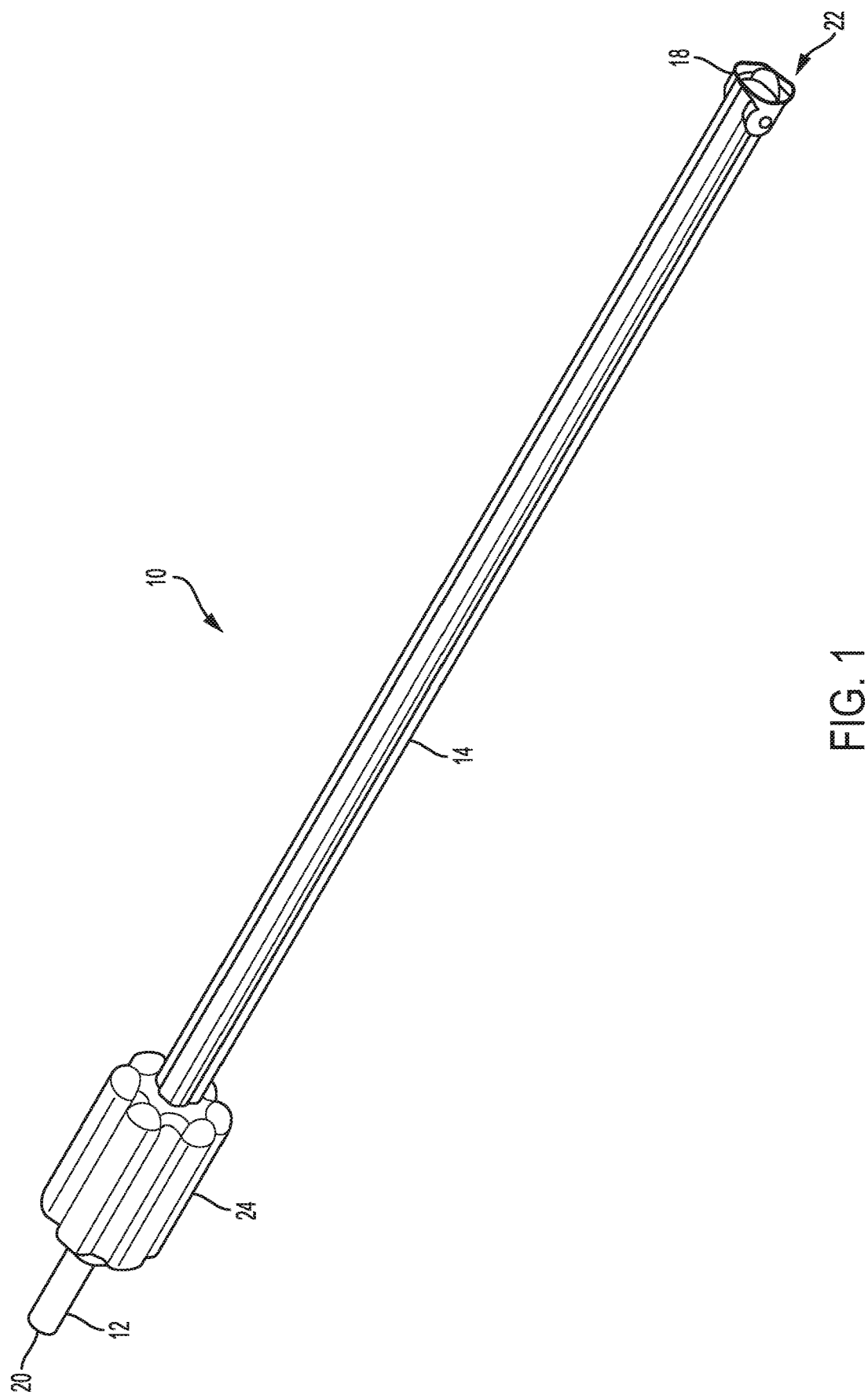
FIG. 1 is schematic of a drill bit according to the present invention.

Referring to the figures, wherein like numeral refer to like parts throughout, there is seen in FIG. 1 a drill bit 10 according to the present invention that can produce a bone tunnel for anchoring of a graft during a surgical procedure with minimal removal of bone. Drill bit 10 comprises shank 12 for mating drill bit 10 with a drill (not show) as is known in the art. For example, shank 12 may allow for drill bit 10 to be coupled to any variety of conventional drills or any future designs. Drill bit 10 further includes a tubular body 14 extending longitudinally along axis X-X from shank 12. Referring to FIG. 2, an inner shaft 16 is positioned within body 14 and extends from shank 12 to a dual position cutting end 22. Body 14 is rotatable about axis X-X relative to inner shaft 16 through at least 180 degrees and is also moveable longitudinally along axis X-X. Body 14 is biased toward cutting end 22 of inner shaft 16. Body 14 terminates in a cam end 18 having a cam surface 20 extending at 45 degrees relative to axis X-X. A handle 24 is secured to body 14 to allow a user to more easily rotate body 14 and move body 14 longitudinally along axis X-X relative to inner shaft 16.

Figure 4:
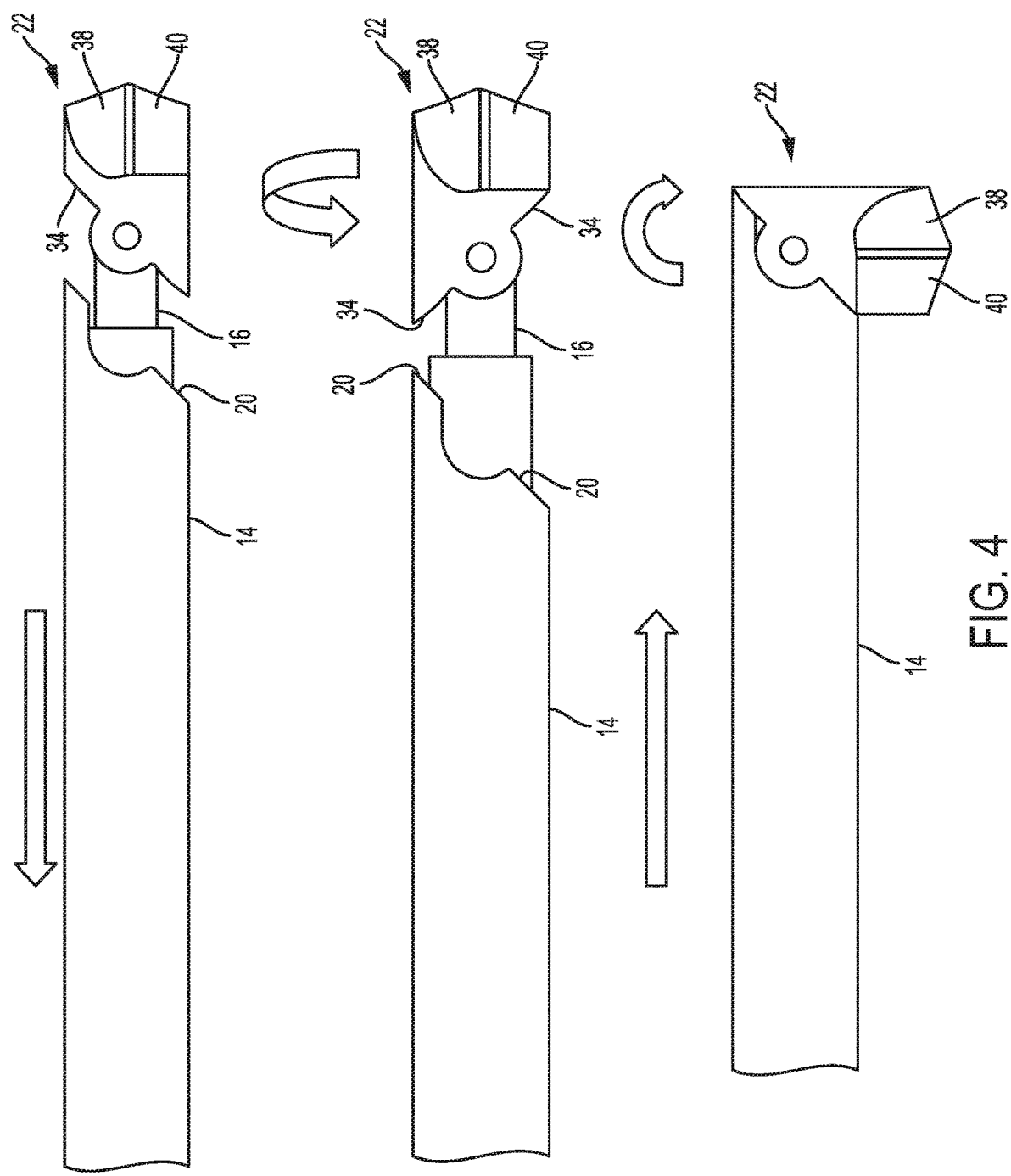
FIG. 4 is a series of schematics of a drill bit according to the present invention illustrating pivoting of the cutting tip between first and second positions.

Referring to FIGS. 2 and 3, a cutting head 30 is pivotally mounted to the end of inner shaft 16 via a pivot pin 32. Cutting head 30 includes a bearing surface 34 having a 45 degree angle relative to axis X-X and thus corresponding to cam surface 20 of body 14 so that cam surface 20 will abut cam end 18 under the bias of body 14. Referring to FIG. 4, withdrawal of body 14 against the bias, followed by rotation of body 14 relative to inner shaft 16 through 180 degrees and then release of body 14 will cause cam surface 20 of cam end 18 to apply a bias to the bearing surface 34 of cutting head 30. Due to the corresponding angles of cam surface 20 and bearing surface 34, body 14 will cause cutting head 30 to pivot about pivot pin 32 until the rotated cam surface 20 of cam end 18 fully aligns with and abuts bearing surface 34 of cutting head 30. As a result, cutting head 30 is moveable between a first position, where cutting head 30 faces longitudinally along axis X-X, and a second position, where cutting head 30 is pivoted 90 degrees from axis X-X to face radially outward.

As seen in FIGS. 2 and 3, cutting head 30 includes a cutting tip 36 having a first cutting surface 38 and a second cutting surface 40 so that cutting tip 36 can perform bone drilling when cutting head is in both the first and second positions. More specifically, cutting tip 36 pivots along with cutting head 30 between a first position, where cutting tip 36 using first cutting surface 38 to form a first bore having a first diameter $d_1$ as drill bit 10 is moved distally along axis X-X, and a second position, where cutting tip 36 using second cutting surface to form a second bore having second diameter $d_2$ that is larger than first diameter $d_1$ as drill bit 10 is moved proximally along axis X-X. Drill bit 10 may thus be configured to form a smaller diameter bore when advanced into a bone, and a larger diameter, second bore (referred to as a reverse counterbore) in the other side of the bone if drill bit 10 is partially withdrawn through the first bore. While cutting tip 36 may be dimensioned to provide first and second bores having any desired diameters, the diameter of first bore preferably corresponds closely to the diameter of body 14 so that body 14 may slide longitudinally within the first bore without precession to maintain the concentricity of the reverse counterbore 52 relative to the first bore.

Figure 5:
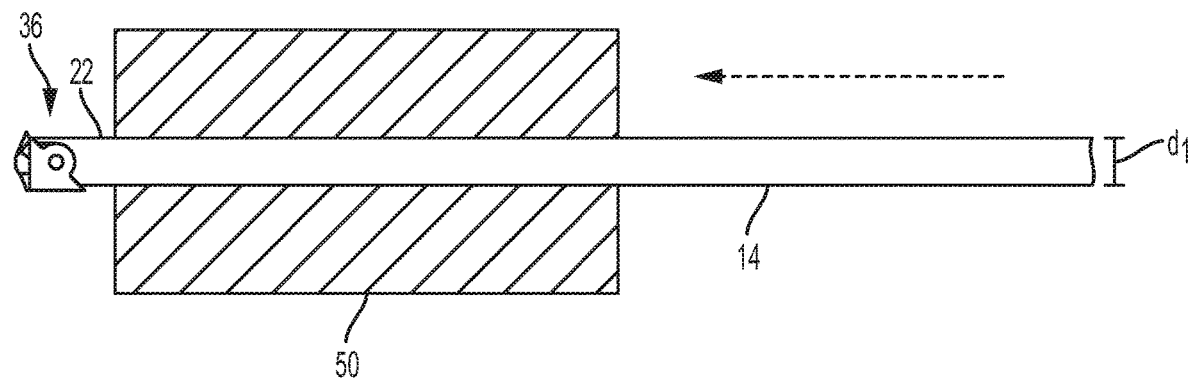
FIG. 5 is a schematic of a drill bit having formed a bone tunnel having a first diameter according to the present invention.
Figure 6:
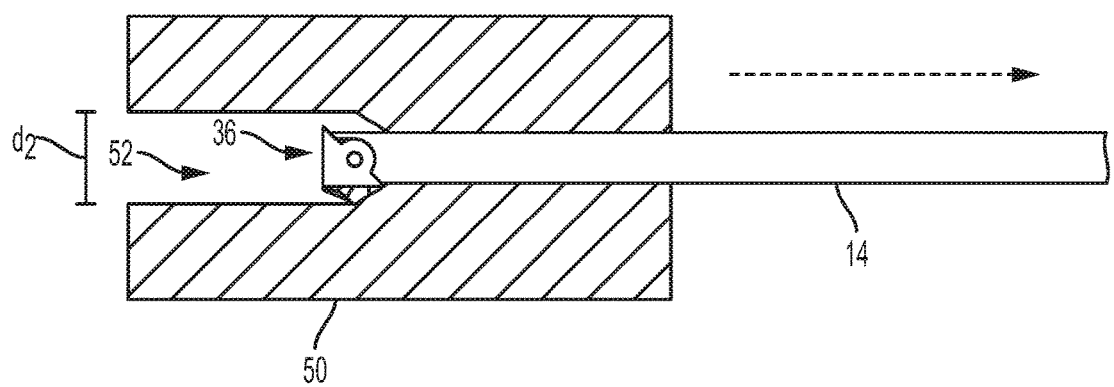
FIG. 6 is a schematic of a drill bit having formed a reverse counterbore bone tunnel having a second diameter according to the present invention.

Referring to FIGS. 5 and 6, drill bit 10 may be advanced through a bone 50 in the antegrade direction with cutting tip 36 in the first position to perform drilling along axis X-X and form a first bore having a first diameter. One cutting end 22 has emerged from the opposite side of the bone, body 14 may be rotated to cause cutting tip 36 to pivot into the second position where cutting tip 36 has pivoted about pivot pin 32 and can form a second bore having a second diameter that is larger than the first diameter of the first bore. Subsequent operation and retraction of drill bit 10 will cause cutting tip 36 to drill a reverse counterbore in the retrograde direction that has the second diameter. Drill bit 10 may then be returned to the first position by withdrawing body 14 relative to inner shaft 16 and then rotating body 14 so that the release of body 14 formed cutting tip 36 to return to the first position. Drill bit 10 may then be removed from the bone 50.

Figure 7:
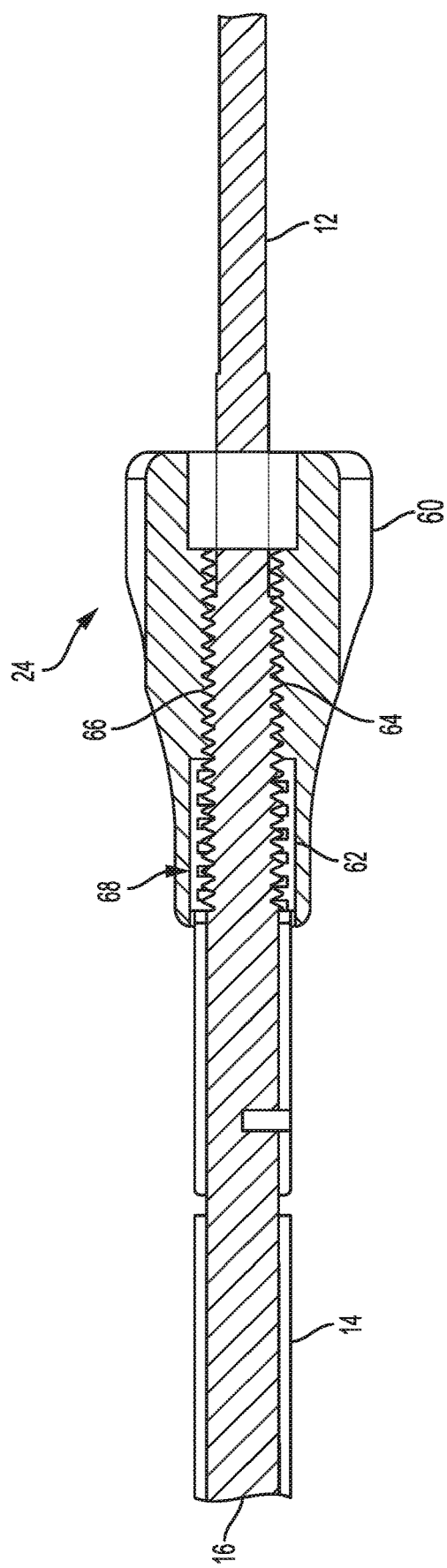
FIG. 7 is a cross-section of an embodiment of a handle for a drill bit according to the present invention.

Referring to FIG. 7, handle 24 of drill bit 10 may include a knob 60 coupled to a compression spring 62 that provides the bias to body 14. Knob 60 is fixed relative to inner shaft 16, such as by complementary sets of threads 64 and 66 so that spring 62 is in a compressed into abutment with body 14. A cavity 68 within knob 60 allows for axial movement of body 14 relative to inner shaft 16 against the bias of spring 62.

Figure 8:
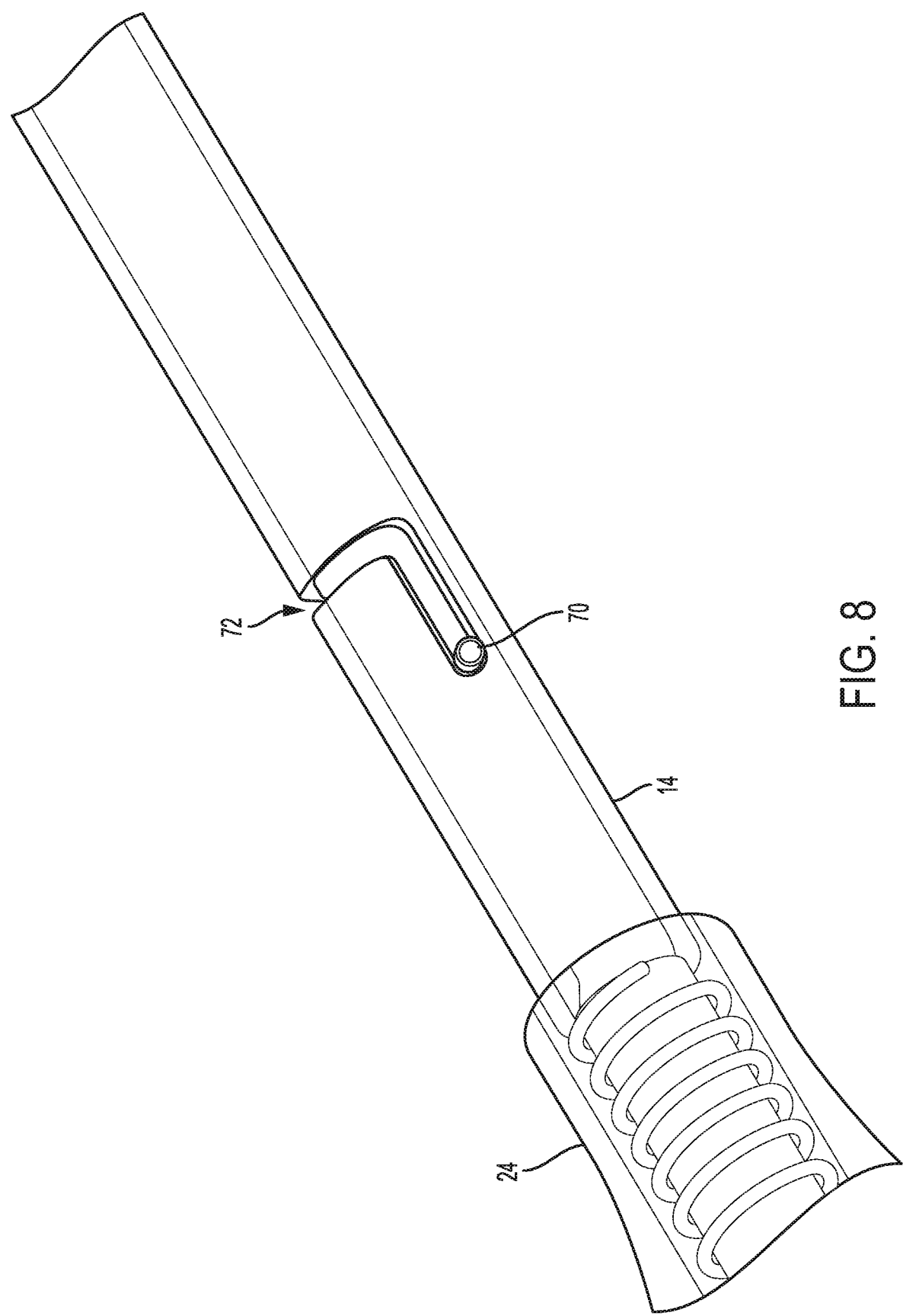
FIG. 8 is a schematic of a pin and track for controlling a drill bit according to the present invention.

Referring to FIG. 8, body 14 may be interlocked with inner shaft 16 via a pin 70 extending radially outwardly from inner shaft 16. A track 72 is formed in body 14 and accepts pin 70 to precisely control the relative movement of body 14 and inner shaft 16 when cutting tip 36 is moved between the first and second positions against the bias of compression spring 62.

Figure 9:
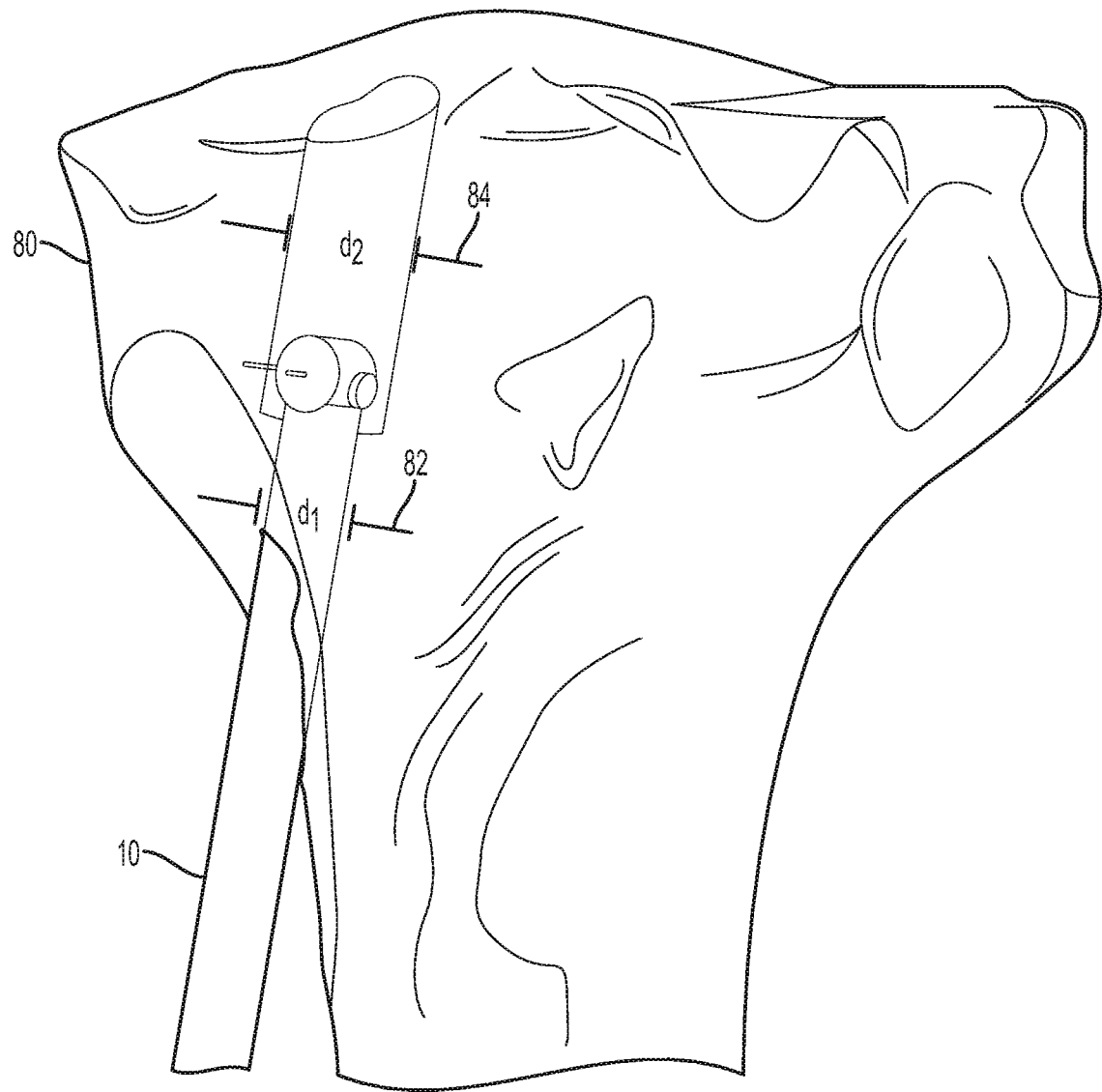
FIG. 9 is a schematic of a knee ligament repair using a drill bit according to the present invention.

Referring to FIG. 9, drill bit 10 may be used for a cruciate ligament reconstruction procedure. Drill bit 10 may be advanced into a bone 80 with cutting tip 36 in the first position to form a pilot bore 82 that is smaller in diameter than conventional procedures. After the pilot bore 82 is formed, cutting tip 36 is then changed into the second position. Drill bit 10 may be driven by a drill and withdrawn partially back through pilot bore 82 to form a second larger diameter bore 84 that is properly dimensioned to accept and secure a ligament graft. In this manner, less bone material is removed from bone 80 during the procedure as only the reverse counterbore of bore 84 is sized to accept the graft.

Figure 10:
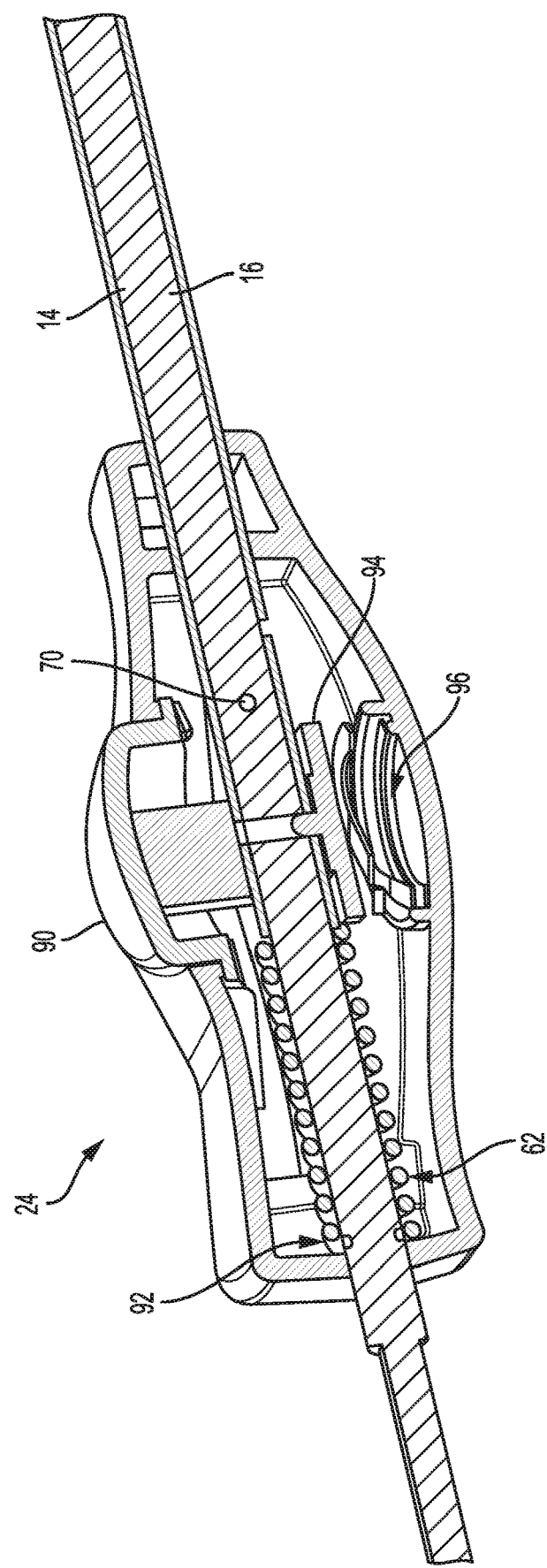
FIG. 10 is a cross-section of another embodiment of a handle for a drill bit according to the present invention.
Figure 11:
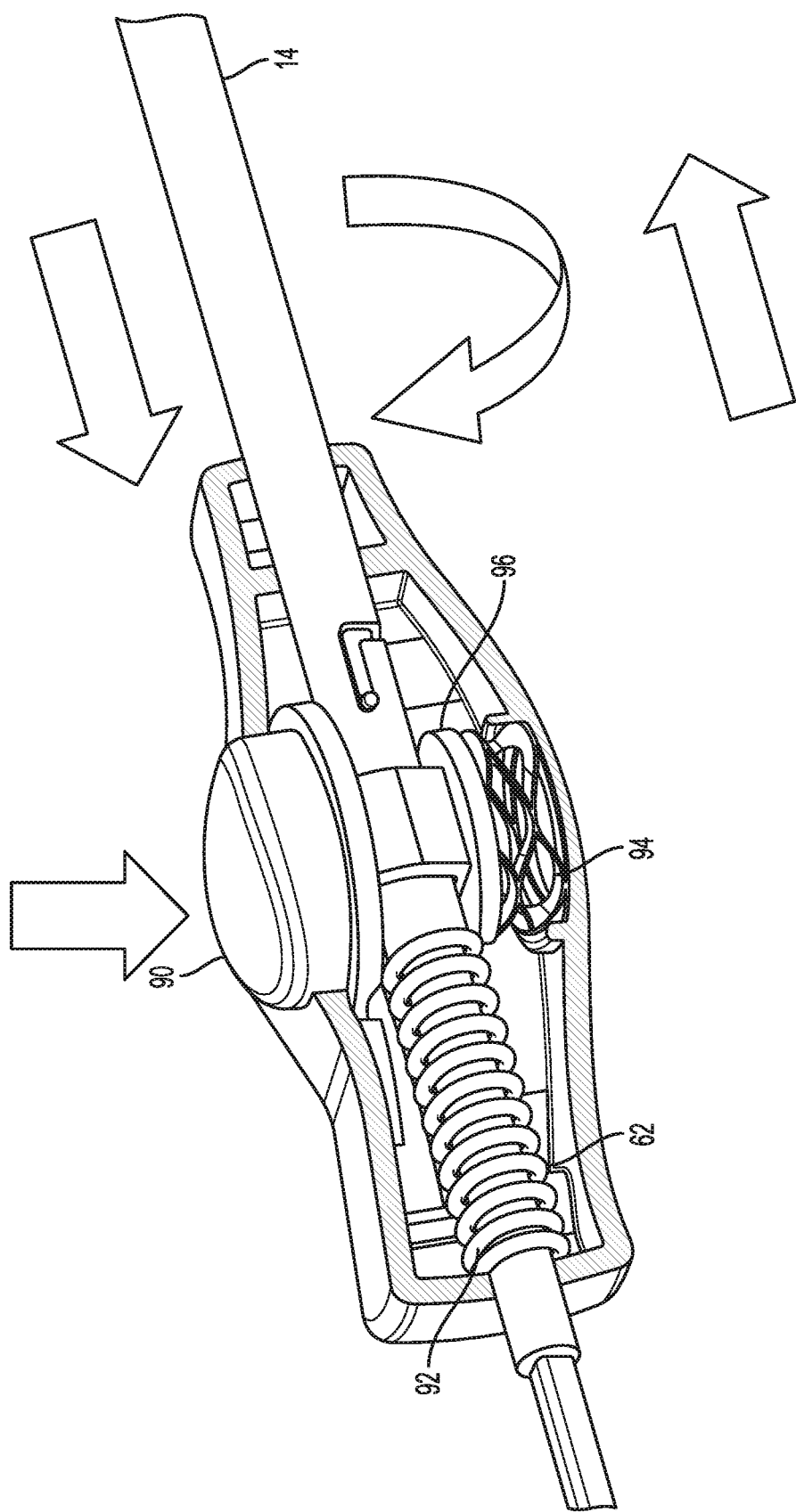
FIG. 11 is a schematic of the operation of the handle embodiment of FIG. 10 according to the present invention.

Referring to FIG. 10, handle 24 may comprise a button 90 coupled to inner shaft 16 by an e-clip 92. Button 90 includes a boss 94 that locks body 14 relative to inner shaft 16 against rotation and axial movement under the bias of a wave spring 96. As seen in FIG. 11, manual depression of button 90 against the bias of spring 96 releases body 14 relative to shaft 16 so that cutting tip 36 can be moved between the first and second positions by the axial and rotational movement of body 14 relative to inner shaft 16 as described above.

Figure 12:
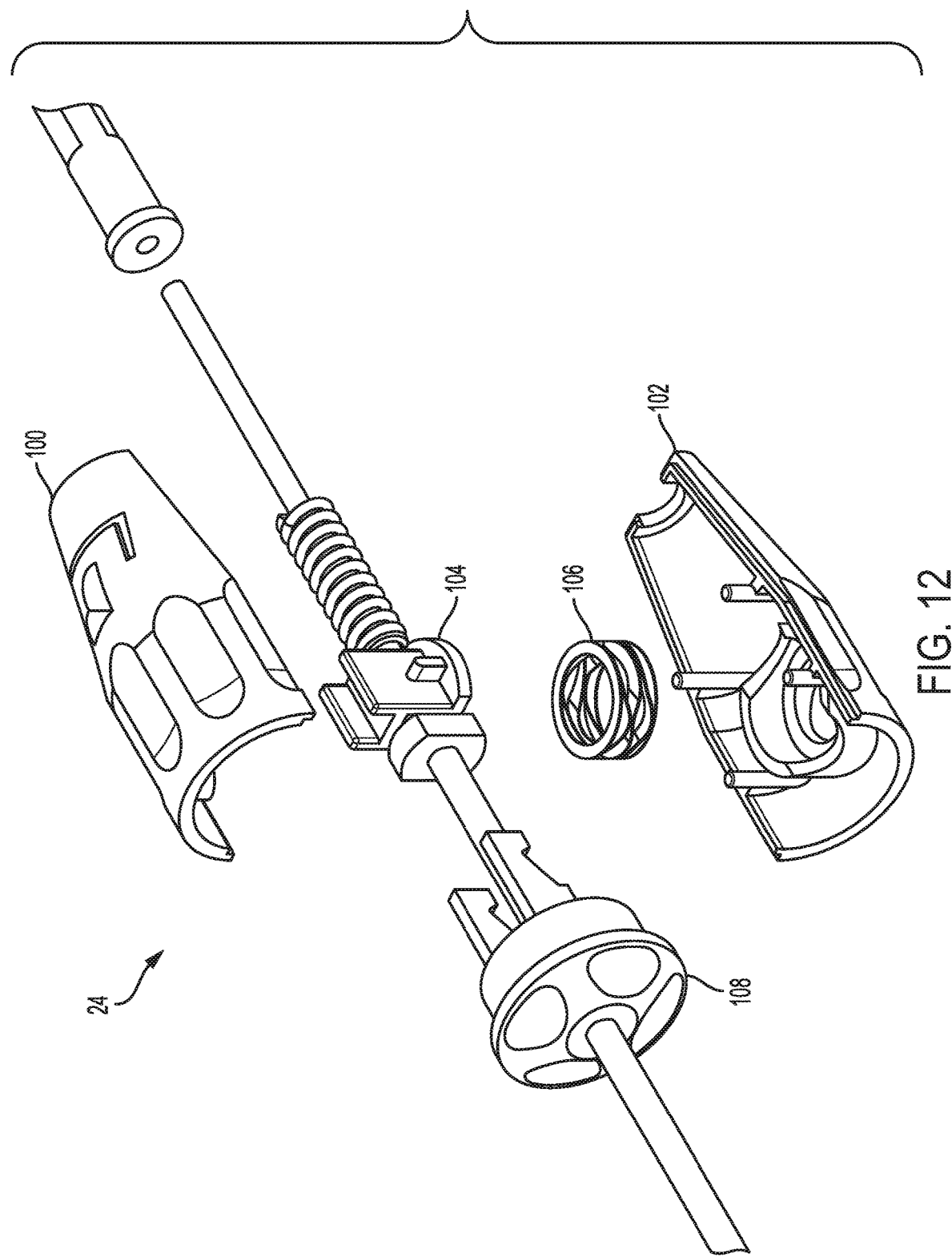
FIG. 12 is an exploded view of a further embodiment of a handle for a drill bit according to the present invention.
Figure 13:
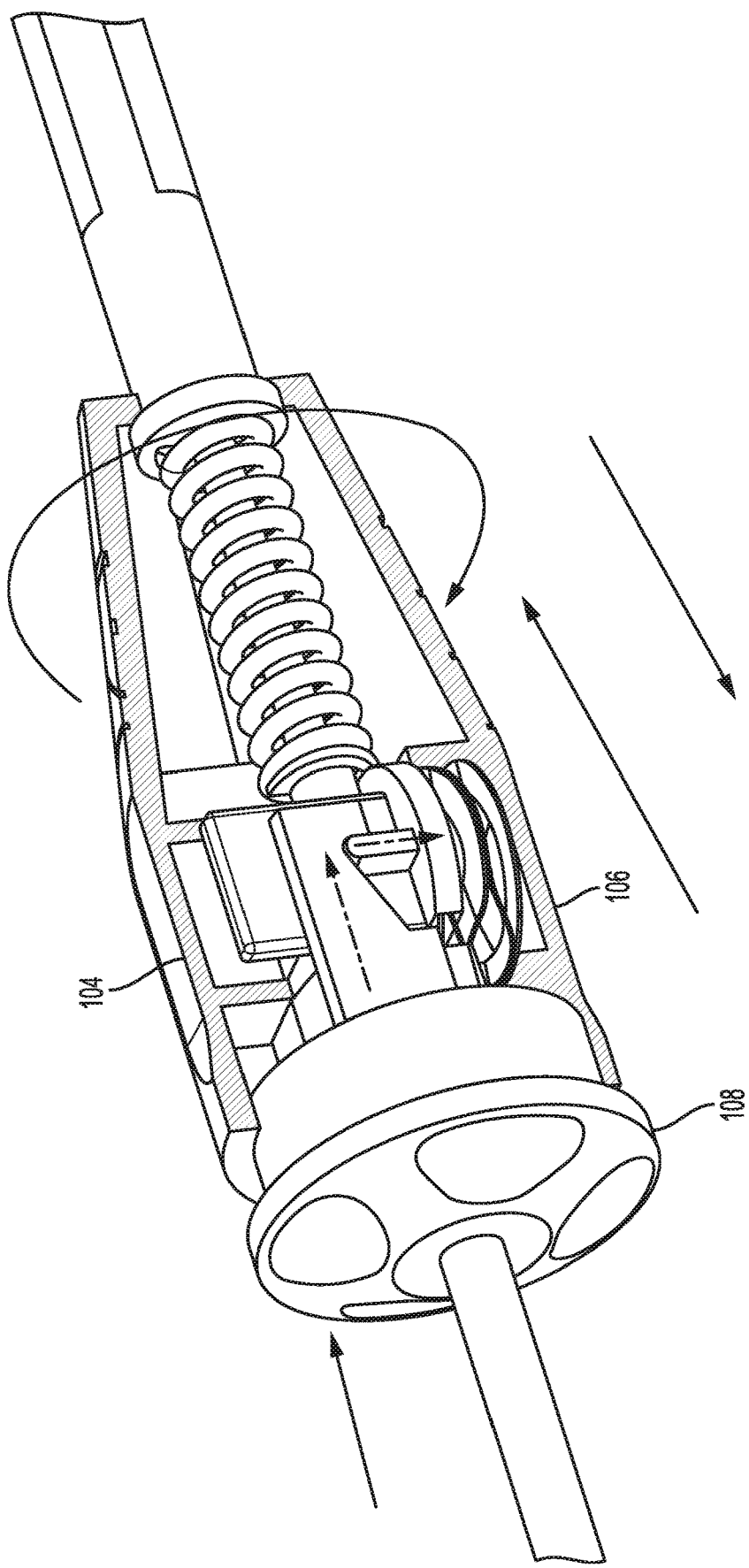
FIG. 13 is a schematic of the operation of the handle embodiment of FIG. 12 according to the present invention.
Figure 14:
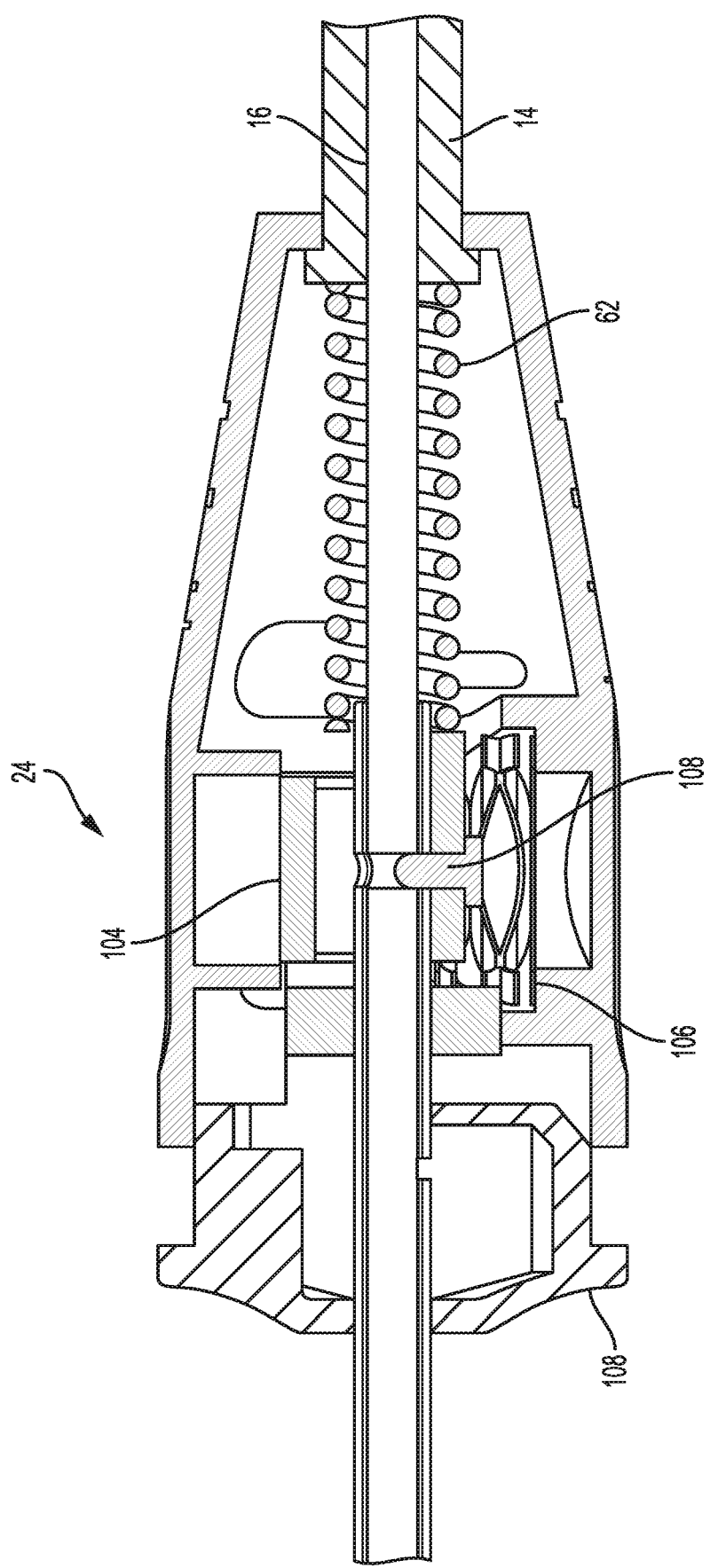
FIG. 14 is a cross-section the handle embodiment of FIG. 12 according to the present invention.

Referring to FIGS. 12 through 14, handle 24 may comprise a housing assembly having top housing 100 and bottom housing 102 that are coupled to body 14 and enclose a lock housing 104. Lock housing 104 is biased by a wave spring 106 to drive a locking pin 108 into of engagement with body 14 and inner shaft 16 to interlock body 14 and inner shaft 16 against axial and rotational relative movement, as seen in FIG. 14. A front cap 110 is moveable axially along body 14 to drive lock housing 104 against the bias of spring 106, thereby unlocking locking pin 108 from body 14 and inner shaft 16 to allow for axial and rotational relative movement. As seen in FIG. 13, the housing assembly may then be moved axially and rotated to move body 14 and thus move cutting tip 36 between the first and second positions as described above.

What is claimed is:

1. An orthopedic drill bit, comprising:
    a shaft extending along an axis and positioned within a body;
    the body being moveable along the axis and rotatable about the axis and including a cam surface extending at a first angle with respect to the axis; and
    a cutting tip pivotally mounted to said shaft and moveable between a first position where said cutting tip is aligned along said axis and a second position where said cutting tip is perpendicular to said axis, the cutting tip including a bearing surface extending at a second angle with respect to the axis that is complimentary to the first angle;
    wherein the body is biased towards the cutting tip with the cam surface of the body being configured to appl a bias to the bearing surface of the cutting tip; and
    due to the first and second angles of the cam surface and the bearing surface, respectively, the cutting tip pivots to the first or second position until the cam surface aligns with and buts the bearing surface.

2. The drill bit of claim 1, wherein said cutting tip in the first position defines a first bore having a first diameter and said cutting tip in the second position defines a second bore having a second diameter that is larger than the first diameter.

3. The drill bit of claim 1, wherein said body is rotatable between a first orientation that moves said cutting tip into the first position and a second orientation that moves said cutting tip into the second position.

4. The drill bit of claim 1, wherein said cutting tip is configured to form the first bore and the second bore.

5. A method of forming a bone tunnel, comprising the steps of:

providing a drill bit having a shaft extending along an axis; a body enclosing the shaft being moveable along the axis and rotatable about the axis and including a cam surface extending at a first angle with respect to the axis; and a cutting tip pivotally mounted to said shaft and moveable between a first position where said cutting tip is aligned along said axis and a second position where said tip is perpendicular to said axis, the cutting tip including a bearing surface extending at a second angle with respect to the axis that is complementary to the first angle, the body being biased towards the cutting tip with the cam surface of the body being configured to apply a bias to the bearing surface;

advancing the drill bit with said cutting tip in the first position to form a first bore having a first diameter through a bone;

moving said cutting tip into the second position after said cutting tip has passed through the bone; and partially withdrawing said drill bit through said first bore in said bone to form a second bore having a second diameter that is larger than the first diameter;

wherein the step of moving said cutting tip into the second position comprises moving said body axially away from said cutting tip, rotating the body 180 degrees, and moving the body axially into contact with said cutting tip such that the cutting tip pivots to the second position where the cam surface aligns with and abuts the bearing surface.

\* \* \* \* \*